United States Patent [19]

Kovacevic

[11] Patent Number: 5,125,270
[45] Date of Patent: Jun. 30, 1992

[54] LOAD SENSOR FOR A HUMAN HAND

[75] Inventor: Nebojsa Kovacevic, Plymouth, Minn.

[73] Assignee: N. K. Biotechnical Engineering Company, Minneapolis, Minn.

[21] Appl. No.: 587,978

[22] Filed: Sep. 25, 1990

[51] Int. Cl.$^5$ .............................................. A61B 5/22
[52] U.S. Cl. ...................................... 73/379; 128/774
[58] Field of Search ............... 73/379, 862.65, 862.66; 128/26, 774; 272/67, 68

[56] References Cited

U.S. PATENT DOCUMENTS

| D. 247,553 | 3/1978 | Breuer | D10/83 |
|---|---|---|---|
| 1,007,410 | 10/1911 | Zachariae | |
| 1,796,216 | 5/1930 | Pettersson | |
| 1,903,352 | 4/1933 | Ramsey | |
| 2,708,367 | 5/1955 | Lusk | 73/379 |
| 3,442,132 | 3/1967 | De Mare | 73/379 |
| 3,672,219 | 6/1972 | Van Patten | 73/379 |
| 3,738,651 | 6/1973 | Norman et al. | 272/67 |
| 3,916,537 | 11/1975 | Gilligan et al. | 35/29 |
| 4,426,884 | 1/1984 | Polchaninoff | 73/172 |
| 4,530,496 | 7/1985 | Smith et al. | 272/68 |
| 4,657,097 | 4/1987 | Griffen | 73/862.65 X |
| 4,674,330 | 6/1987 | Ellis | 73/379 |

Primary Examiner—Reinhard J. Eisenzopf
Assistant Examiner—E. Shopbell
Attorney, Agent, or Firm—Kinney & Lange

[57] ABSTRACT

A human hand load sensor is a strain gauge based force measurement instrument that has two platforms or handles that can be moved together with parts of the human hand, for example, a thumb and finger, or the handles can be grasped between the heel of the hand and several fingers. The instrument permits very precise measuring of strength force by supporting a movable handle relative to a base or reference handle through a flexure system which deforms predictably under shear loading as the handles or platforms are moved together. The flexure system is much like a parallel linkages made from a single block of material between a base and a movable block, and having a small deflecting beam sensing element between the base and the movable block that is isolated from influences of bending or rolling movements on the strain level. The strain energy is sensed with strain gauges that provide a signal directly proportional to the shear loading for very accurate measurements. The making of the base and movable block portions from a single block of material eliminates assembly joints, giving a greater repeatability, high linearity, less zero shift during use, less hysteresis, and more stable calibration coefficients. Further, the machining process or manufacturing process is relatively low cost and highly accurate. The one piece body is easy to calibrate. The base or platform size can be modified quite easily for a wide variety of uses.

13 Claims, 4 Drawing Sheets

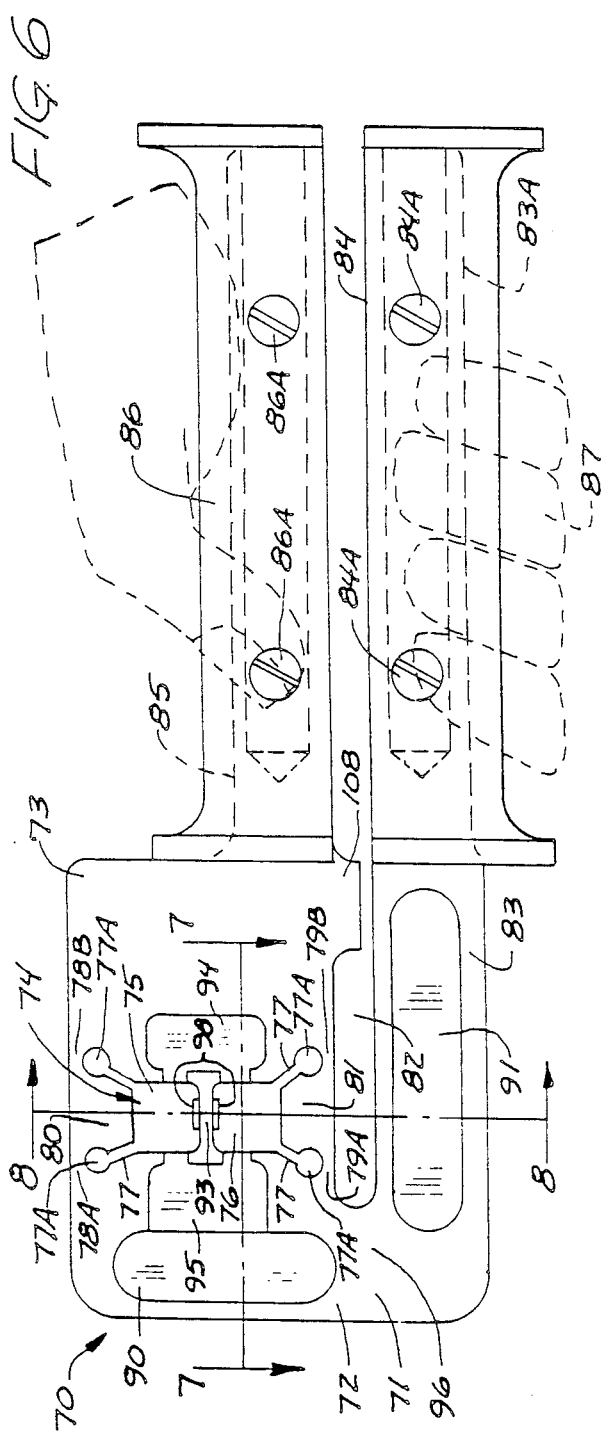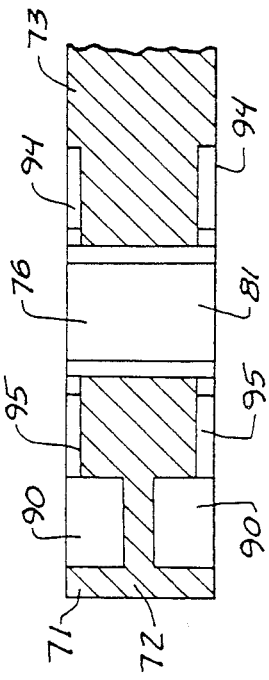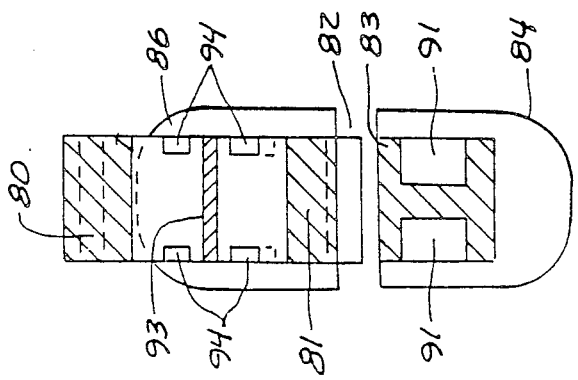

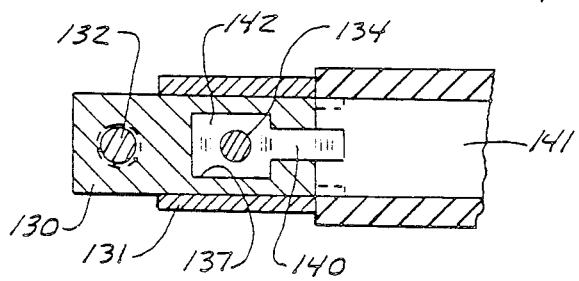
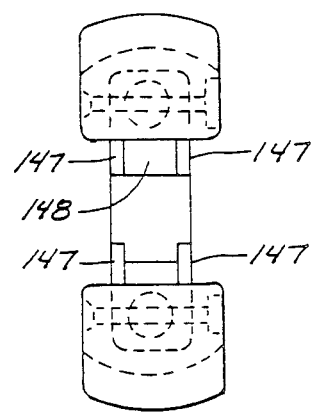
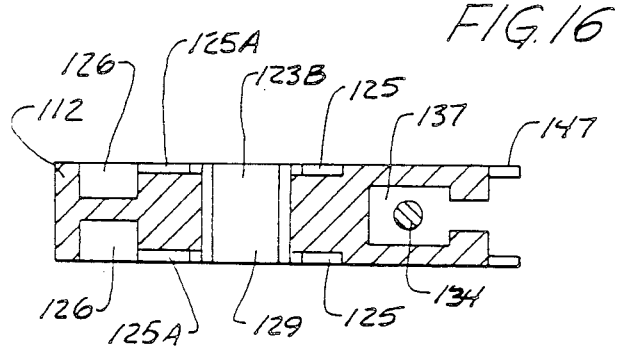
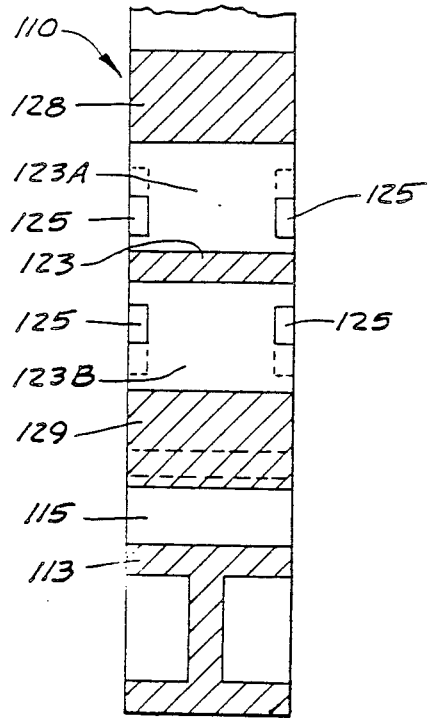

LOAD SENSOR FOR A HUMAN HAND

BACKGROUND OF THE INVENTION

The present invention relates to a hand load sensor that is precise, easily used, and which permits analysis of forces exertable by a hand for evaluation and rehabilitation. In the prior art, measurement of grip and pinch strength has been recognized as being desirable. U.S. Pat. No. 4,674,330 illustrates a sensor with a structure that has a pair of bending beams mounted onto a support, which can be bent toward each other. The beams themselves have strain gauges for sensing the bending moments in the beams, but accuracy is always in question. In particular, assertions stating that forces measured at a constant distance are proportional to forces applied anywhere to the structure are inaccurate given normal application of the sensor. Under normal applications, loads applied to the sensor cause elastic deformation of the structure where the strain gauges are located. This elastic deformation contributes to deflection of associated handles as the load is applied which, in turn, causes the sensor to respond non-linearally. In addition, elastic deformation causes twisting moments to appear that are not fully isolated by the strain gauges, while mechanical joints, such as interconnections of the handles with a slider, introduce hysteresis and non-repeatability to the sensor's performance.

A simplified exercising machine which provides gripping or pinching exercises is shown in U.S. Pat. No. 1,007,410. It is designed primarily as an exercise device for piano players. A design patent showing a hand dynamometer is U.S. Pat. No. 247,553 which has a type of indicator dial, and what appears to be a pair of handles that can be squeezed together. A force measuring instrument which can be grasped and used for measuring forces through hydraulic pressure is shown in U.S. Pat. No. 2,708,367. An electric dynamometer utilizing strain gauges on a centrally mounted beam for measuring grasping force between two parallel handles is shown in U.S. Pat. No. 3,442,132.

U.S. Pat. No. 3,672,219 illustrates a grasping device that also operates on a hydraulic principal and displays measured force leads on a gauge. While the hydraulic type gauges eliminate mechanical pivots, they generally are large, not particularly accurate, and they are subject to problems that are associated with leakage of hydraulic fluid.

A hand grip testing machine that can be used as an amusement device, and which utilizes mechanical links shown in U.S. Pat. No. 1,903,352. Other patents which illustrate the general state of the art include U.S. Pat. Nos. 4,530,496; 3,738,651; 1,796,216; 3,916,537 and 4,426,884. These patents show various types of force sensors, but none of these show the unique mounting structure of the present invention which provides for a wide range of force determinations with high accuracy, good repeatability, and little zero shift.

SUMMARY OF THE INVENTION

The present invention relates to a force measurement instrument that has a reference handle or platform, and a movable handle or platform that are mounted so that they can be manually moved together with either a pinch force or grasp force and an output indicating the force exerted is obtained. The movable handle and the reference handle are connected through a flexure mounting that eliminates mechanical joints but which permits accurate measurement of shear loading induced deflection of a beam connected between the two relatively movable parts.

The flexure arrangement essentially is a pair of links that act substantially similar to parallel links when the movable platform or handle is moved relative to the reference platform or handle so that the handles tend to remain parallel to each other. The force can be determined by using strain gauges on a deflecting beam. The level of forces sensed can be adapted to a wide range using the same general flexure construction for mounting the movable handle or platform relative to the reference handle or platform, and extraneous bending and rolling moments are isolated from the sensing beam that is used.

In some forms of the invention, the spacing between the reference platform and the movable platform can be quickly and readily adjusted to suit the existing conditions and the different types of grasping or pinching tests being conducted. The basic configuration also can be adapted for permitting measurement of the forces of a hand grasp or grip, by having the platforms formed into suitable handles. These handles can be made adjustable either by having a kit with different size handles for accommodating different size hands, or by having one of the handles adjustable relative to the other. The output from the strain gauge bridge can be provided through suitable electronics either with digital readout meters or by providing inputs to dedicated software for recording a patient's progress.

Accurate measurements across a wide range of forces can be obtained with very little deflection due to the unique mounting of the movable platform or handle relative to the reference platform or handle.

BRIEF DESCRIPTION OF THE DRAWINGS

FIG. 6 is a side elevational view of a modified form of the invention comprising a grasp sensor;

FIG. 7 is a fragmentary sectional view taken as on line 7—7 in FIG. 6;

FIG. 8 is a sectional view taken as on line 8—8 in FIG. 6;

FIG. 14 is an end view of the handle portions of FIG. 13;

FIG. 15 is an fragmentary sectional view taken as on line 15—15 in FIG. 13;

FIG. 16 is a sectional view taken as on line 16—16 in FIG. 13; and

FIG. 17 is an enlarged fragmentary sectional view taken as on line 17—17 in FIG. 13.

DETAILED DESCRIPTION OF THE PREFERRED EMBODIMENTS

Figure 1:
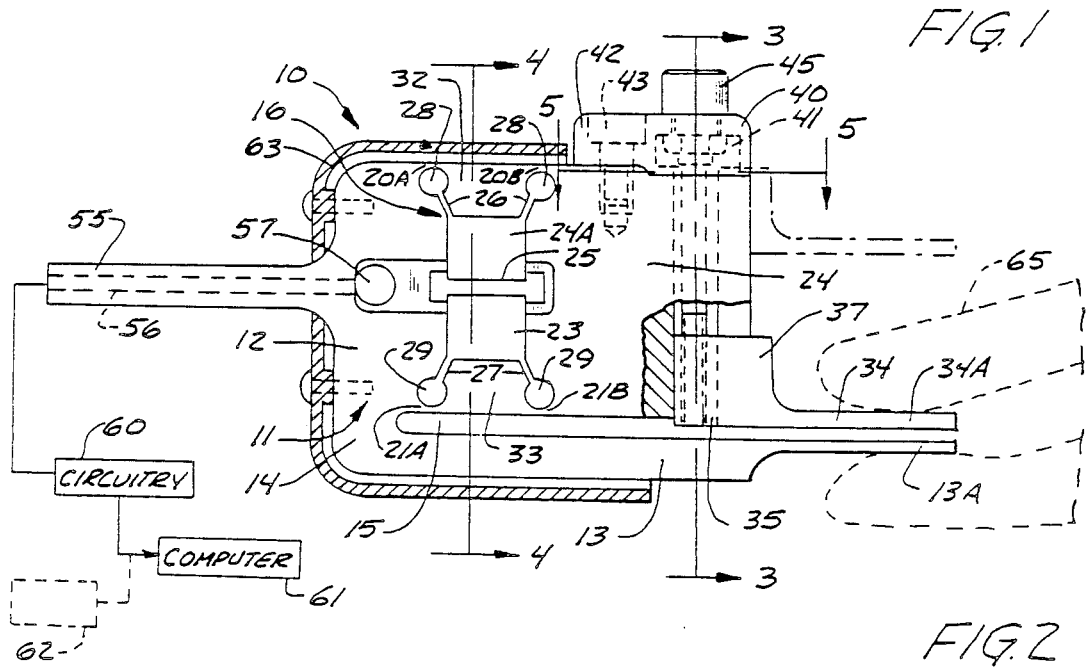
FIG. 1 is a side elevational view of a first form of the invention comprising a pinch sensor, with parts and section parts broken away.
Figure 2:
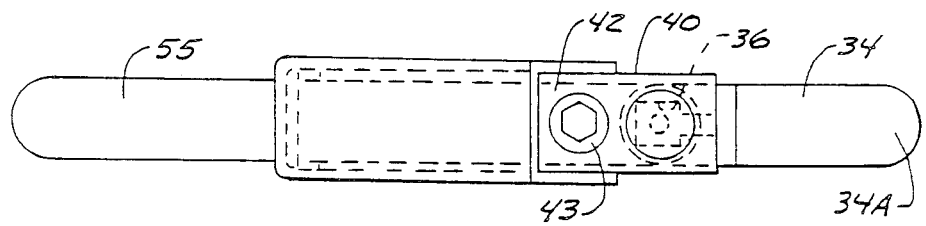
FIG. 2 is a top plan view of the device of FIG. 1.
Figure 3:
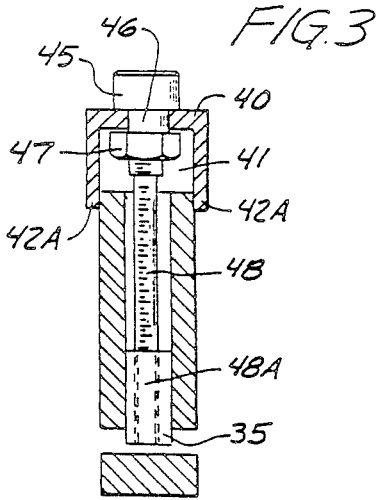
FIG. 3 is a sectional view taken as on line 3—3 in FIG. 1.
Figure 5:
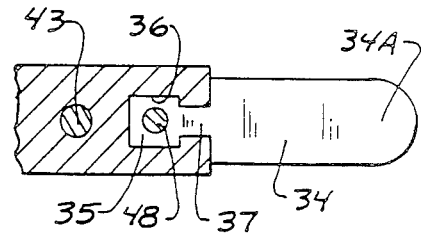
FIG. 5 is a fragmentary sectional view taken as on line 5—5 in FIG. 1.

A first form of the hand load sensor, comprising one portion thereof is a finger pinch strength sensor indicated generally at 10 which comprises a main body 11 that is divided into a base portion 12 which includes a reference handle or platform 13 that is integrally mounted to the base portion 12 by a web 14, and is divided out from the unitary body 11 with a slot 15 that extends inwardly from a remote end 13A of the reference platform or handle 13. A flexure hinge assembly indicated generally in the region 16 is formed in the body 11 and separates the base portion 12 from a movable mounting block portion 24 of the body. The flexure hinge assembly 16 is an integral parallel link assembly formed by thin hinge sections 20A and 20B at the top end, as can be seen, and 21A and 21B at the lower end. The hinge sections are formed by forming openings indicated at 23 and 24A in the body 11, on opposite sides of a flexure sensing beam 25 that is along the center line of the body. Then slots 26 and 27 are formed at the top and bottom of the body which join with cross openings 28 and 29, at the top and bottom to leave the integral thin hinge sections 20A, 20B, 21A and 21B. In other words, all the material of the body 11 is removed in the portions 23, and 24A at the slots 26 and 27, as well as the cross openings 28 and 29. The thin hinge sections 20A and 20B, and 21A and 21B thus form hinges for essentially parallel connecting flexure links or beams 32 and 33, respectively that serve to join the movable mounting block 24 to the base portion 12 of the body 11. The mounting block 24 is used for mounting a movable handle or platform 34 that has an end portion 34A that is parallel to the end portion 13A of the reference platform or handle 13. The movable platform or handle 34 is a relatively flat plate like member that has a mounting block 35 integrally formed therewith and, as can be seen in FIG. 5, the mounting block 35 fits within a guide slot 36 in the block 24. A tang 37 joins the mounting block 35 to the outer end portion 34A of the movable handle or platform 34. The slot 36 is formed in the block 24 to hold the block 35 and it has a narrow portion through which tang 37 extends. A cap member 40 is mounted to the upper side of the mounting block 24 above the guide slot 36. As can be seen in FIGS. 1, and 3, the cap 40 has an interior bore or recess 41 at one end, and has a mounting end member 42 at an opposite end that rests on the top of the mounting block 24 and is held in place with a cap screw 43. The recess 41 forms side wall members 42A that rest along the outside of the upper part of the mounting block 24 and when the cap screw 43 is tightened down, the cap 40 is held securely in place.

Referring to FIG. 3, a movable platform adjustment screw 45 has a shank portion 46 rotatably mounted in the top wall of the cap member 40. The opening for the shank 46 in the top wall of the cap member 40 aligns with the center of the slot 36, and the shank portion 46 is made of sufficient length so that a nut 47 can be threaded onto a thread section of the adjustment screw 45 and tightened against the bottom surface of the shank 46 and the screw 45 will be free to rotate relative to the top wall of the cap 40. The screw 45 has a threaded end 48 that threads into a suitable threaded bore 48A in the block member 35, so that upon turning the screw 45, the block member 35 can be raised and lowered to change the spacing between the reference platform 13A and the movable platform 34A. The extreme position is the separated position of the platform or handles 34 and 13 shown in dotted lines in FIG. 1.

Figure 4:
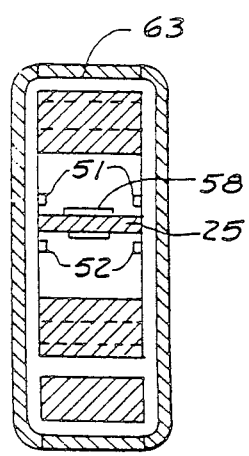
FIG. 4 is a sectional view taken as on line 4—4 in FIG. 1.

The sensing beam 25 is machined in place, so that the body 11 remains one piece of material including the sensing beam 25, so that there are no mechanical joints joining the block 24 to the base portion 12, only flexure joints. There are recesses shown at 51 and 52 around the ends of the beam where it joins the movable block portion 24 and base portion 12, respectively, as can be seen in FIG. 4. A separate handle 55, for manually holding the body when it is being used as a pinch sensor or force sensor, is integrally formed with the base portion 12 on an opposite side of the body from the reference handle 13. The handle 55 can have an interior bore shown in dotted lines at 56 that opens through a cross hole 57 so that wiring for strain gauges indicated generally at 58 in FIG. 4 and which are mounted on the beam 25 can have suitable circuitry connected to them. Signal circuitry 60 can be provided, and the outputs can be connected to a computer 61 or a digital readout 62, as an option.

An outer case 63 is shown in cross section in FIG. 1, which is used for shielding the internal flexure assembly 16.

It can be seen that when a hand indicated generally and schematically at 65 is used for determining pinch strength, between digits of the hand as shown, a thumb and finger, the reference platform portion 13A will be engaged by one of the digits, and the other movable platform portion 34A will be squeezed by the other digit tending to try to reduce the gap between the two handles or platforms. This will cause the block 24 to move substantially parallel to its original position and cause the shear loading that is transferred by the hinge members 20A, 20B and 21A, 21B to the beam 25 causing the shear loading to exert bending on the beam 25 and thereby activating the strain gauges, which will indicate the amount of force applied. Because the platforms 34 and 13 are connected to each other through an integral flexure assembly, integrally made from one piece, relative deflection of the platforms or handles does not have to be very great, and the flexures isolate the sensing beam 25, so that there is essentially no influence of bending or rolling movements on the strain level due to the type of loading between the finger tips. The reference platform 13 is an integrate part of the one piece body 12 as well, and the movable platform or handle 34 is equipped with a mechanism for allowing a continuous adjustment of the spacing between the two platforms to accommodate different and hand size. The mechanical assembly, has no mechanical pivots and thus provides greater repeatability, enhanced linearity, less zero shift, much less hysteresis, and less change in calibration coefficients. Further, the base can be machined quickly and easily, as well accurately, from one piece of aluminum or other suitable metal so that precise measurements are possible across a wide range of compression.

The finger tip sensor that is shown in FIGS. 1-5 can measure "key pinch", as shown in FIG. 1, and well as lateral pinches between fingers, a tip pinch, and tripod pinch, and other types of pinching functions of the hand. The accurate measurement of forces of these functions of the hand are critical in diagnosis, treatment and rehabilitation, and the adjustability feature allows the use of the device in the measurement of pinch strength for small children and adults with extreme limitation due to injury or disease. The handles or platforms can be modified with use with infants in an effort to measure very early pinch capacity.

The tang or handle 55 permits the examiner to hold the unit during testing, to facilitate its operation.

By way of example of the size the vertical height of the body 11 is in the range of 2 inches, and the overall length from the surface where cover 63 rests to the end of the stationary platform 13 is about 3¾ inches. The range of load of a typical device such as this would be from 0 to 12 kilograms with resolution of about 0.003 Kg.

The excitation of the strain gauges can be using any desired type of circuitry.

As a second form of the set of human hand assessment devices, a grasp sensor is shown in FIGS. 6 through 12. The grasp sensor is indicated generally at 70, and comprises unitary body 71 that has a base portion 72, and a movable block portion 73 joined together with a flexure assembly 74. The flexure assembly 74 is formed by cutting out openings 75 and 76, and slots 77 at the corners of the openings 75 and 76 leading to bores 77A which form thin hinge sections 78A and 78B, and 79A and 79B for providing the flexure support for the movable block portion 73.

The thin hinge sections 78A and 78B separate out a connecting flexure link or beam 80, and the thin hinge section 79A and 79B separate out a parallel connecting flexure link or beam 81, which join the movable mounting block 73 to the base portion 72 of the body 71. The mounting block 73 mounts a movable handle or platform 85 that is integrally machined with the movable block 73, and is covered with a handle grip 86 and held in place with suitable screws 86A. A reference handle of platform 83 is separated out by a slot 82 from the movable block 73 and portions of the stationary block 72. It is supported on the stationary block 72, and forms a reference grip portion 83A that has a handle grip 84 mounted thereon and held in place with screws 84A.

The reference handle 83 permits a hand indicated in dotted lines at 87 to grasp the handle grips and tend to squeeze the movable handle or platform 85 toward the stationary handle or platform 83, in the portions housed with the grips 84 and 86.

The mounting block 72 has weight reducing recesses 90 on the sides thereof, and the reference handle or platform 83 has recesses 91 on the sides thereof, as well, as can be seen in FIG. 8.

The reference handle or platform 83 is joined to the base portion 72 through a web portion 96 that is formed when the slot 82 is formed out of the stationary or reference handle or platform 83. The openings 75 and 76 separate out at sensing flexure beam 93 that is integrally joined to the base portion 72 and movable block 73. The beam is machined out by cutting out the openings 75 and 76. Shallow recesses 94 and 95 are formed along the opposite side surfaces of the base and movable blocks as can be seen in FIG. 7.

In this form of the invention, the mounting web 96 is heavier than the mounting web in the first form of the invention because the sensor 70 is a grasp sensor and more power can be generated. In this form of the invention, the handles or platforms 83 and 85 are both integrally formed, so that there can be no adjustment movement of the movable handle relative to the reference handle. The movable handle or platform 85 moves relative to the reference handle or platform 83 through the flexure 74 when force is applied tending to close the two handles together. When a load is applied by grasping with the hand such as that shown at 87 schematically, the mounting block 73 will tend to move parallel to its original position because of the hinge action at hinges 78A, 78B, 79A and 79B which separate out flexure links or beams 80 and 81 that act as parallel links. This movement will bend the sensing beam 93. The beam 93 can have suitable strain gauges thereon which are shown only schematically at 98, and suitable leads can extend from these strain gauges to a circuit, such as that shown in the first form of the invention in FIG. 1. The beam 93 will again be subjected to bending that is dependent upon shear forces, without unwanted bending or rolling moments. The flexure hinges 78A, 78B, 79A and 79B tend to isolate the beam from unwanted forces.

By grasping the unit and squeezing the handles 83 and 85 together, suitable readings can be taken. The one piece or integrally formed body and handles eliminate all assembly joints, resulting in a better overall performance, specifically in relation to repeatability, linearity, zero shift and improved hysteresis. Further, there is less change in calibration coefficients where there are no mechanical joints. The machining process is less expensive than for multi part sensors, and the unit is relatively easily calibrated.

Figure 9:
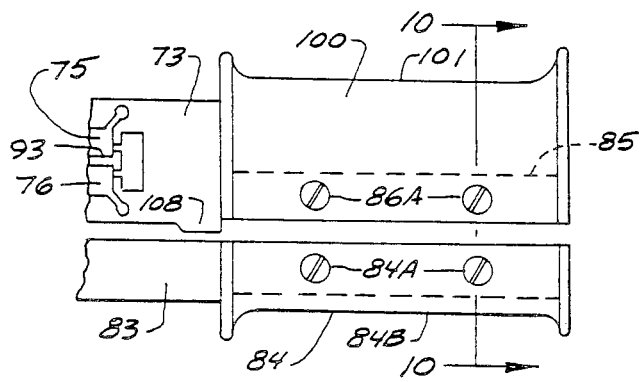
FIG. 9 is a fragmentary side view of a modified handle formed as part of a kit and used with the device of FIG. 6.
Figure 10:
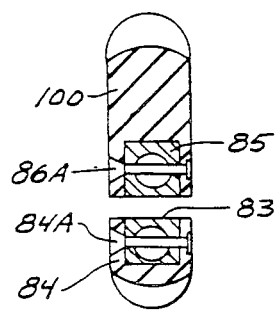
FIG. 10 is a sectional view taken as line 10—10 in FIG. 9.

In order to accommodate different size hands, a kit of handles is provided. A first size handle is shown in FIG. 6, and also shown in end view in FIG. 8 behind the cross sectional portions of the sensor. In FIGS. 9 and 10 a maximum size unit is shown for the largest hands. In this form of the invention, the handle grip 86 is removed. The screws 86A have recessed heads and nuts, and when they are removed, the handle grip 86 can be removed and a maximum size handle grip 100 put into its place. It has a recess that fits around the movable handle or platform 85 as can be seen in FIG. 10. The handle grip 84 remains in place, and the platform 83, which is the reference platform that is integrally formed at the base portion 72 of the sensor, supports handle 84 as before. It can be seen at the upper surface of the handle 100, indicated generally at 101 is spaced a substantially a greater distance from the under surface of handle 84, which is indicated in FIG. 9 at 84B, so that a large hand can still be used for grasping the handle assembly and for measuring the loads exerted.

Figure 11:
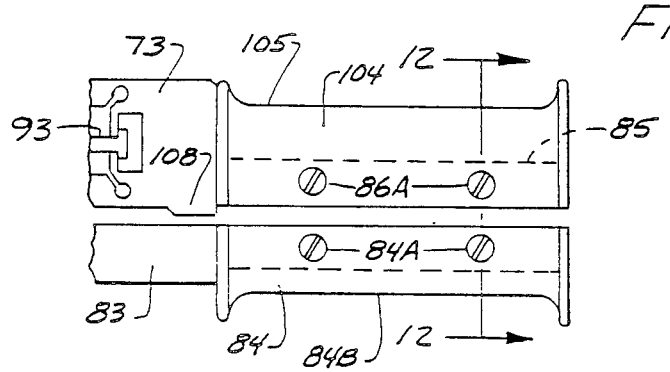
FIG. 11 is a fragmentary side view similar to FIG. 9 showing a different size handle in place and forming a different size grip.
Figure 12:
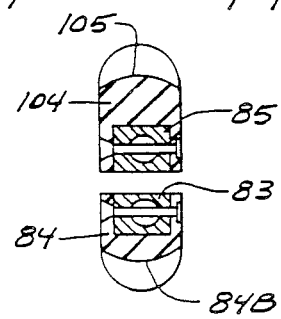
FIG. 12 is a sectional view taken as on line 12—12 in FIG. 11.

In FIGS. 11 and 12 a medium size handle member 104 is used in place of the handle 86, and fits over the movable platform or handle 85 which is integral with the movable block 73. The cap screws 86A can be removed and replaced and place the handle 104 in position. The upper surface 105 of the handle 104 is spaced an intermediate distance from the lower surface 84B of the reference handle 84 as can be seen.

It should also be noted that a stop block 108 can be provided on the movable block 73 to avoid overstressing the flexure assemblies, and still provide adequate motion for grasp sensing.

The handle grips 86, 100, and 104 form part of a kit for the grasp sensor, and can be interchanged as desired for the test.

A third form of the invention which is also a grasp sensor, is shown in FIGS. 13-17, and in this form of the invention, the movable handle of the grasp sensor is adjustable substantially the same manner as the handle for the first form of the invention or the pinch sensor.

Figure 13:
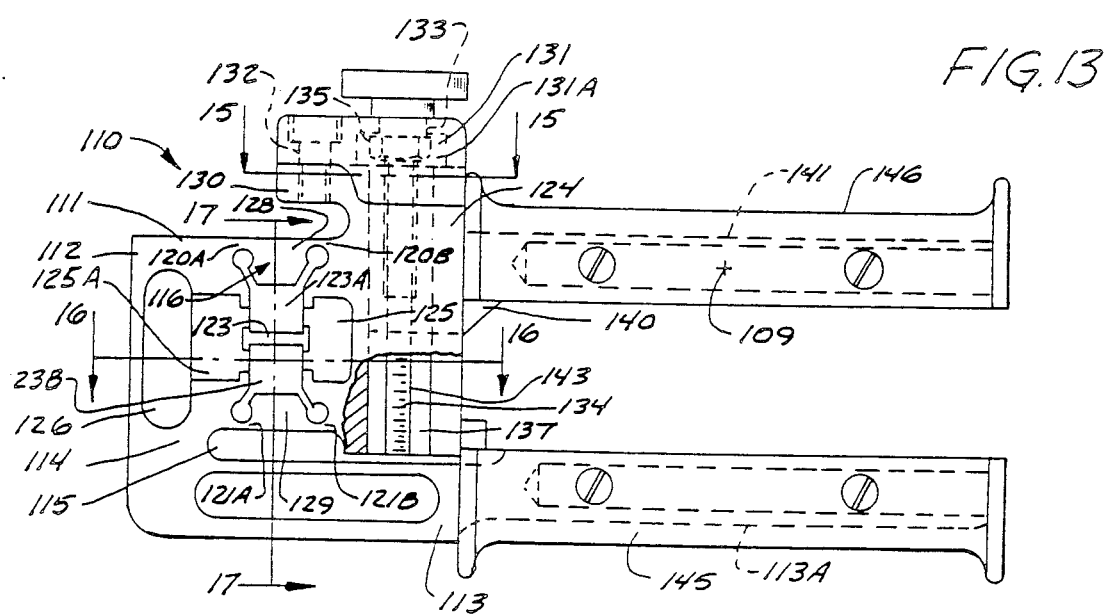
FIG. 13 is a side elevational view of a further modified form of the invention illustrating an adjustable movable platform grip for measuring grasping forces by a hand.

In FIG. 13, the grasp sensor 110 includes a body member 111 that has a base portion 112. A reference handle or platform 113 is integrally formed with the base portion 112. The reference platform or handle 113 is connected to the base portion of the body 111 through a web 114. A slot 115 separates out the reference handle or platform from the body 111. A movable block portion 124 is connected to the base portion 112 through a flexure 116, which has hinge connections formed at hinge points 120A and 120B and 121A and 121B. A flexure beam 123 is separated out by openings 123A and 123B as before, and is supported at its ends at recessed portions 125A and 125 of the main body, and the main body also can have a relief recess 126 formed into the sides thereof.

The movable block 124 is connected through the parallel link arrangement using flexure links or beams 128 and 129, which are separated out by openings 123A and 123B, as previously explained. The movable block 124 has an overhanging top lip 130 that mounts a cap 131 that has a surface held tight against the upper surface of the movable block 124 with a suitable cap screw 132, as previously explained. The cap 131 has a recess 131A forming a top wall that rotatably mounts a shank 133 of an adjustment screw 134 that is held in place in the cap 131 with a suitable lock nut 135. The shank portion 133 rotates in the opening in the cap 131 when the lock nut 135 tightly holds the screw 134 in place.

The screw 134 extends along a vertical slot 137 formed in the movable block 124. Slot 137 is T-shaped, as can be seen in FIG. 15, and the slot slidably receives a movable platform or handle assembly 140. The movable platform assembly 140 has an outwardly extending handle or platform end 141, and a mounting block 142 that is slidably mounted in the vertical slot 137. The screw 134 has a threaded end portion 143 that threads through a bore in the block 142, and upon rotating the screw 134, the movable platform or handle 141 can be raised or lowered relative to the stationary handle 113, and its outer end portion 113A.

The reference platform or handle 113A has a handle grip 145 mounted thereon, and this is of a normal size. The movable handle or platform 141 has a handle grip 146 mounted thereon so that it can be grasped by a hand in the manner shown in FIG. 6. The spacing of the movable platform 141 from the stationary platform section 113A can be adjusted by rotating the screw 134 to accommodate different size hands. The cap 131 is essentially similar to cap 40 shown in the first form of the invention.

Thus the device shown in FIGS. 13-17 provides for rapid handle adjustability and also provides a high load grasp sensor that will accommodate a wide range of loads. It should be noted that there are small guide tabs 147 that fit along the opposite sides of a gusset portion 148 (see FIG. 14) of the movable handle or platform assembly 140 as the unit comes closer to the reference handle or platform 113A.

The operation of the grasp sensor shown in FIGS. 13-17 is the same as that previously explained, and the movable block 124 will move substantially parallel as movable handle or platform 141 is moved towards the reference handle or platform 113A. The loading will bend the beam 123 without the influence of bending moments and/or torsion. The movement that is sensed by the beam 123 will be substantially sheer movement that causes the beam to bend. Suitable strain gauges can be provided on the beam 123 and used with an electronic circuit as explained in connection with the first form of the invention.

The grasp sensor shown in FIGS. 13-17 does provide for adjustability of the grasp size, utilizes a movable block that is unitary with the base and reference handle or platform so that the sensor beam is isolated from unwanted moments and forces by the flexure assembly. The strain gauges on the sensing beam 23 provides a high output with a small deflection. Sensing can be done in a conventional manner, and with the reference platform or handle being an integral part of the one piece body, there are no mechanical hinges which cause hysteresis, and the construction enhances repeatability, linearity, with less zero shift and easy calibration. The machining also is fairly rapid even with the adjustable handle. Accurate measurements of the forces of functions, such as the grip strength of the human hand, are critical for diagnosis and treatment for rehabilitation of injured hands. The separation of the handles between the upper surface of the movable grip on the movable handle to the lower surface of the fixed or referenced grip on the reference handle, ranges from about $1\frac{3}{4}$ to $2\frac{3}{4}$ inches. The guides 147 forms stops for the movable handle as it is threaded toward the reference handle and its minimum size position, so that it will not contact the reference handle, but will always be stopped at a minimum spacing for operation.

The load on the grasp sensors are usually from about 0 to 70 kilograms, with a resolution of approximately 10 grams. Accuracy is very good, with tolerances plus or minus 0.15% for full scale operation.

The grasp sensors are lightweight, inasmuch as the mounting blocks are usually made of aluminum, and will provide repeatability and operability across a wide range of conditions. By way of reference, the main body 111 has a vertical height shown in FIG. 13 in the range $2\frac{1}{2}$ inches, while the overall length is in the range of 7 inches. The handle grips are generally about 4 3/8 inches in overall length. The grasp sensor is made so that the center point 109 of the grip mentioned in longitudinal direction is assumed the load point for calibration and force indication.

Accuracy and reliability of the present invention are preserved by isolating the sensor beam between parallel collecting links which prevents first order bending and torsional moments from appearing on the sensor beam. This structure allows the sensor beam to be more responsive to primary shear loading without compromising ultimate rigidity and elastic deformation of the handles while the load is applied. This is accomplished with three parallel flexures connecting the two movable parts. The center flexure is a beam that carries the sensing strain gauges which provide an output signal proportional to strain. In FIG. 1, the flexures are 32, 33 and 25, which is the sensing beam. In FIG. 6, the flexures are 80, 81 and 93 and in FIG. 13, the flexures are 128, 129 and 123. Furthermore, forming the above structure from a unitary block portion without mechanical joints creates an ideal system that is less susceptible to hysteresis, creep, and zero shift; while, at the same time, allowing the sensor to be easily made and less expensive to produce.

Although the present invention has been described with reference to preferred embodiments, workers skilled in the art will recognize that changes may be made in form and detail without departing from the spirit and scope of the invention.

What is claimed is:

1. A load sensor apparatus for a human hand and digits thereof for determining loads exerted between two portions of such hand comprising a sensor including a body, said body having a base portion and a reference platform fixably mounted to said base to provide for engagement with one portion of a hand to be tested; said body having a movable block portion, and flexure members connecting said movable block portion to said base of said body, and a movable platform mounted on said block portion and positioned adjacent said reference platform whereby two portions of a hand to be tested can engage the reference platform and movable platform at the same time and cause movement of the movable platform toward the reference platform, and means for measuring the movement of the movable block portion relative to the base portion of the body.

2. The apparatus of claim 1 wherein said flexure members comprise a unitary pair of straps connected between the base portion and movable block portion with multiple hinge points that form parallel connecting straps, whereby when the movable platform is moved toward the reference platform the movable block portion remains substantially parallel to its original position, and a beam member between said movable block portion and base portion that is loaded in shear when the movable platform is moved toward the reference platform, the means to measure movement being sensitive to the amount of shear in said beam.

3. The apparatus is specified in claim 2 wherein said movable block portion includes means for slidably mounting said movable platform, and means for adjusting the position of the movable platform on the block portion relative to the reference platform.

4. The apparatus as specified in claim 2 wherein there are four hinge points.

5. The apparatus as specified in claim 1 wherein said movable platform has a hand grip member mounted thereon on a side of the movable platform opposite from the reference platform, said hand grip member being removable, and a kit containing a plurality of hand grip members that have different spacings from the exterior thereof to portions of the grip which engage the movable platform in direction measured away from said reference platform.

6. The apparatus as specified in claim 3 wherein said adjustable means comprises a guide slot on said block portion, and wherein said movable platform has a guide block mounted in said guide slot, and means to threadably move said guide block in direction along said guide slot for adjustably positioning the movable platform.

7. The apparatus as specified in claim 1 wherein said flexure member, said base portion and said block portion of said body are all machined from a single block of material.

8. The apparatus as specified in claim 1 wherein said reference platform is attached to said base portion, and extends adjacent to, but spaced from the block portion outwardly from said base portion to an operative position.

9. The apparatus as specified in claim 1 wherein said reference platform and said movable platform comprise generally flat strap members adapted to be loaded by digits of a hand.

10. The apparatus as specified in claim 1 wherein said reference platform and movable platform comprise members adapted to be grasped between a heel of a hand and the fingers of the hand to load the movable platform toward the reference platform.

11. An assembly for measuring loads comprising a unitary block of material, said unitary block having a base portion partially separated from a movable portion of said unitary block by a slot, said base portion having a first platform, and said movable portion of said unitary block having a second platform, said second platform being adjacent to and separated from said first platform by said slot, opening means formed on the movable portion of the unitary block to form first and second block portions and to form a flexure joining the first and second block portions, the flexure comprising spaced apart links, each joined to the first and second block portions through integral hinge sections, and an integral beam positioned between the links and joined to the first and second block portions, the beams deflecting from shear loading when the first and second block portions are moved relative to each other, when a loading is applied to said platforms causing said platforms to deflect towards each other, and means for sensing deflection of the integral beam.

12. A load sensor apparatus for a hand and digits thereof for determining loads exerted between two relatively movable portions of such hand comprising a sensor including a body, said body having a base portion, support means on the base portion to provide for engagement with one portion of a hand to be tested; said body having a movable block portion, flexure members connecting said movable block portion to said base portion of said body, a platform mounted on said block portion and positioned to receive a second portion of a hand to be tested when one portion is engaging the support means so that gripping between the two portions causes movement of the platform toward the support means and means for measuring the movement of the moveable block portion relative to the base portion of the body.

13. The apparatus of claim 12 wherein said flexure members comprise a unitary pair of straps connected between the base portion and movable block portion with four hinge points that form parallel connecting straps whereby when the platform is moved toward the support means the movable block portion remains substantially parallel to its original position, and a beam member between said movable block portion and base portion that is loaded in shear when the platform is moved toward the support means, the means to measure movement being sensitive to the amount of shear in said beam.

* * * * *